United States Patent [19]

Sikorski et al.

[11] 4,405,356

[45] Sep. 20, 1983

[54] ESTER DERIVATIVES OF N-ARYLSULFINYL-N-PHOSPHONOME-THYLGLYCINATES AS HERBICIDES

[75] Inventors: James A. Sikorski, West Lafayette, Ind.; Mary A. Hoobler, Creve Coeur, Mo.

[73] Assignee: Monsanto Company, St. Louis, Mo.

[21] Appl. No.: 298,057

[22] Filed: Aug. 31, 1981

[51] Int. Cl.³ .................... A01N 57/22; C07F 9/40
[52] U.S. Cl. .................................. 71/87; 260/941; 260/968; 549/221

[58] Field of Search .................... 260/941; 71/87; 549/221

Primary Examiner—Anton H. Sutto
Attorney, Agent, or Firm—Gordon F. Sieckmann; Raymond C. Loyer

[57] ABSTRACT

Ester derivatives of N-arylsulfinyl-N-phosphonomethylglycinates useful as herbicides. Also disclosed is a process for preparing the same, herbicidal compositions containing the same and herbicidal methods employing such glycinates as herbicidal compositions.

27 Claims, No Drawings

ESTER DERIVATIVES OF N-ARYLSULFINYL-N-PHOSPHONOMETHYL-GLYCINATES AS HERBICIDES

This invention relates to novel ester derivatives of N-arylsulfinyl-N-phosphonomethylglycinates which are useful as herbicides. This invention further relates to a process for preparing the same, to herbicidal compostions containing the same and to herbicidal methods employing such compounds and compositions.

U.S. Pat. No. 4,067,719 issued to Gerard A. Dutra on January 10, 1978 discloses N-phosphonomethylglycinonitriles of the formula

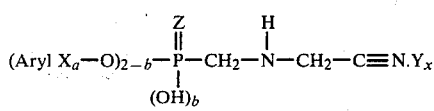

wherein (Aryl) is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 2, provided that x must be zero when b is 1, as well as a process for producing such compounds. These N-phosphonomethylglycinonitriles are said to be useful as herbicides.

U.S. Pat. No. 4,008,296 issued to John Edward D. Barton on Feb. 15, 1977 describes ester derivatives of N-phosphonomethylglycinonitrile having the formula

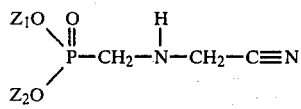

wherein $Z_1$ and $Z_2$ each represent an alkyl radical of from 1 to 6 carbon atoms; which are said to be useful as herbicides.

U.S. Pat. No. 4,252,554 issued to Gerard A. Dutra et al on Feb. 24, 1981 discloses compounds of the formula

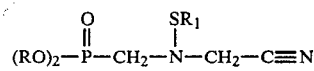

wherein R is phenyl, naphthyl or biphenylyl or phenyl, naphthyl or biphenylyl substituted with from 1 to 3 substituents independently selected from the class consisting of lower alkyl, lower alkoxy, lower alkylthio, alkoxycarbonyl, methylenedioxy, trifluoromethyl, cyano, nitro and halogen; and $R_1$ is phenyl or phenyl substituted with from 1 to 3 substituents independently selected from the class consisting of lower alkyl, lower alkoxy, halogen, trifluoromethyl and nitro.

The compounds of the present invention are represented by the formula

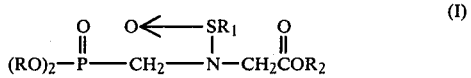

wherein R of this invention is selected from the group consisting of phenyl, naphthyl, biphenylyl; or phenyl, naphthyl or biphenylyl substituted with from 1 to 3 substituents independently selected from the group consisting of hydrogen, lower alkyl, lower alkoxy, methylenedioxy; $R_1$ is independently phenyl or phenyl substituted with from one to three substituents selected from the group consisting of lower alkyl, lower alkoxy, halogen, trifluoromethyl and nitro; and $R_2$ is lower alkyl or araloweralkyl.

Illustrative of the substituted phenyl groups which R and $R_1$ represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethyl-phenyl, nitrophenyl, methylthiophenyl, butylthiophenyl, cyanophenyl, ethoxycarbonylphenyl, and the like, and di- and tri-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of substituted naphthyl represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methyl-b-biphenylyl, nitrobiphenylyl, bromobiphenylyl, dimethylbiphenylyl, difluorobiphenylyl, trimethylbiphenylyl and the like.

As employed herein, the term "lower alkyl" designated alkyl radicals which have from 1 to 4 carbon atoms in a straight or branched chain, such as, for example, methyl, ethyl, propyl, isopropyl, butyl, isobutyl, sec-butyl, and t-butyl.

As employed herein, the term "araloweralkyl" includes combinations of those groups as aforedefined for the term "lower alkyl" with aryl groups such as phenyl, benzyl, naphthyl and biphenylyl.

Typical groups representative of araloweralkyl include phenylmethyl, phenylethyl, phenylpropyl, phenylbutyl and the like.

It is preferred that R is phenyl or phenyl substituted with lower alkoxy; that $R_1$ is independently phenyl or phenyl substituted with lower alkyl; and that $R_2$ is independently lower alkyl or aralower alkyl.

Preferably, R is independently phenyl or methoxyphenyl; $R_1$ is independently phenyl, methylphenyl, and $R_2$ is independently methyl, ethyl or phenylmethyl.

In accordance with the present invention, N-phosphonomethylglycinates of formula (I) are prepared by reacting a compound of the formula

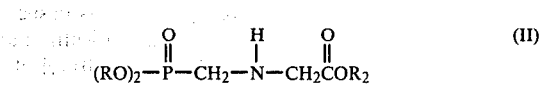

wherein R and $R_2$ are as above defined, in an aprotic solvent, with an aryl sulfinyl chloride of the formula

 (III)

wherein $R_1$ is as above defined, in the presence of a hydrogen chloride acceptor and at a reaction temperature necessary to initiate and sustain the aforedescribed reaction. The reaction temperature is in the range from about 0° to about 100° C. However, for ease of reaction and recovery of product, it is preferred to conduct the process of the present invention within a temperature range of about 10° to about 50° C.

In preparing the novel glycines of formula (I), the ratio of reactants is not narrowly critical. For best results, however, for each mole of a compound of formula (II), one should employ one mole of an aryl sulfinyl chloride of formula (III) to produce one mole of a glycine compound of formula (I). It is preferred to employ an excess of aryl sulfinyl chloride of formula (III) for ease of reaction and maximum yield of product. A hydrogen chloride acceptor is preferably used in the aforedescribed reaction in stoichiometric excess to insure completeness of reaction.

The hydrogen chloride acceptor is typically an amine, preferably a tertiary amine, which is inert with the reactants employed or the products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline mixtures thereof and the like.

Due to the reactive nature of the various reaction intermediates and reactants, for best results, the process of the present invention should be conducted in an aprotic solvent under essentially anhydrous conditions. Illustrative of acceptable aprotic solvents which may be employed in the process of this invention include benzene, methylene chloride, toluene, tetrahydrofuran, cyclohexane, methylcyclohexane, hexane, octane, dioxane, ethyl ether mixtures thereof and the like.

While the processes of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

In each of the following examples the particular aryl sulfinyl chloride employed as a reactant, e.g. benzene sulfinyl chloride and p-toluene sulfinyl chloride respectively, was prepared by generally following a method described in "A Superior Method For Preparing Sulfinyl Chlorides", Journal of Organic Chemistry, Vol. 33, pp. 2104–2108 (1968), Irwin B. Douglass and Richard V. Norton which is incorporated herein in its entirety by reference. The aforementioned method is based on chlorination of a mixture of alkyl or aryl disulfide and acetic anhydride to yield the desired arylsulfinyl chloride and acetyl chloride.

PREPARATION OF BENZENE SULFINYL CHLORIDE 21.8 g (0.1 mol) of freshly recrystallized diphenyl disulfide was slurried in 18.8 ml (0.2 mol) of distilled acetic anhydride in an oven dried 250 ml sidearm round bottom flask. The resulting mixture was cooled to a temperature of −10° C. in a dry ice-water-ethylene glycol bath. Then over a 10 minute period 8 ml of liquid chlorine was added to the mixture. The mixture became a clear orange solution which was stirred for 15 minutes. Additional liquid chlorine was added in 1 ml portions until the solution turned from orange to greenish-yellow. The total amount of liquid chlorine added was about 15 ml. The solution was stirred at −10° C. for 1½ hours. The solution was removed from the bath and the acetyl chloride was distilled off under reduced pressure employing a water aspirator while allowing the solution to warm to room temperature. When bubbling of the solution had ceased, the flask was disconnected from the aspirator and connected to a vacuum pump for ½ hour at room temperature. The temperature of the solution was increased to 40° C. for about another ½ hour. The flask was disconnected from the vacuum pump and the yellow contents of the flask were weighed (31.8 g.) The yellow contents were placed under vacuum at 40° C. for an additional 20 minutes to give 31.75 g (95%) of a brown liquid. This brown liquid, benzene sulfinyl chloride, was dissolved in toluene and diluted to 50 ml of solution for later use.

GENERAL PROCEDURE OF EXAMPLES 1, 2 AND 3

A glyphosate reactant (0.03 mol) was dissolved in 150 ml of toluene in an oven-dried 250 ml flask that had been cooled under nitrogen. Triethylamine (0.03 mol) was added as a hydrogen chloride acceptor. A solution of benzene sulfinyl chloride (0.03 mol) prepared as described above in toluene as an inert solvent was slowly added dropwise via syringe to the glyphosate reactant and triethylamine in toluene. When the addition was complete, the reaction mixture was stirred at room temperature overnight. $^{31}P$ NMR indicated complete uptake of starting glyphosate material. The precipitate of triethylamine hydrochloride was removed by filtration. The toluene filtrate formed during filtration was adsorbed onto silica gel and purified by HPLC on a 1"×4' silica gel column to give the desired glyphoste sulfinamides. $^1H$ and $^{31}P$ NMR, FDMS, and elemental analysis were all consistent with pure product material.

EXAMPLE 1

In this example Glycine, N-[(diphenoxyphosphinyl)-methyl]-, methyl ester was employed as a glyphosate reactant to prepare glycine, N-[(diphenoxyphosphinyl)-methyl]-N-(phenylsulfinyl)-, methyl ester as a yellow oil $n_D^{24.5}$ 1.5753, in 56% yield, corresponding to a compound of Formula (I) wherein R and $R_1$ are phenyl and $R_2$ is methyl. The analysis was:

Calculated: C, 57.51; H, 4.83; N, 3.05; S, 6.98; Found: C, 57.47; H, 4.87; N, 3.04; S, 6.95.

EXAMPLE 2

In this example, Glycine, N-[[Bis(4-methoxyphenoxy)phosphinyl]methyl]-, ethyl ester was employed as a glyphosate reactant to prepare glycine, N-[[bis(4-methoxyphenoxy)phosphinyl]methyl]-N-(phenylsulfinyl)-, ethyl ester as a yellow oil $n_D^{24.5}$ 1.5647, in 73% yield, corresponding to a compound of formula (I) wherein R is methoxyphenyl, $R_1$ is phenyl and $R_2$ is ethyl. The analysis was:

Calculated: C, 56.28; H, 5.29; N, 2.62; S, 6.01; Found: C, 56.28; H, 5.33; N, 2.63; S, 6.01.

EXAMPLE 3

In this example, Glycine, N-[(Diphenoxyphosphinyl)methyl]-, phenylmethyl ester was employed as a glyphosate reactant to prepare glycine, N-[(diphenoxyphosphinyl)methyl]-N-(phenylsulfinyl)-, phenylmethyl ester as a yellow oil $n_D^{25}$ 1.5689, in 59% yield, corresponding to a compound of formula (I) wherein R and $R_1$ are phenyl, and $R_2$ is phenylmethyl. The analysis was:

Calculated: C, 62.80; H, 4.89; N, 2.62; S, 5.99; Found: C, 62.82; H, 4.94; N, 2.59; S, 5.91.

PREPARATION OF P-TOLUENE SULFINYL CHLORIDE 24.6 g (0.1 mol) of freshly recrystallized p-tolyldisulfide was slurried in 18.8 ml (0.2 mol) of distilled acetic anhydride in an oven-dried 250 ml sidearm round bottom flask with magnetic stirring bar and a stopcock connector. The resulting reaction composition was cooled to $-10°$ to $-20°$ C. in a water-ethylene glycol-dry ice bath. All transfers and reactions in this example occurred under nitrogen blanket. About 7 ml of chlorine was condensed at $-78°$ C. and transferred by cannula over 15 minutes to the reaction composition. The reaction composition became a clear bright orange solution and then the orange color began to fade. Additional chlorine was added in 1 ml portions until the solution turned to a greenish-yellow color. The solution was stirred at $-10°$ C. for 1 hour and acetyl chloride was distilled off under reduced pressure employing a water aspirator while allowing the solution to return to room temperature. Bubbling of the solution ceased after about 45 minutes and the solution was connected to a vacuum pump for ½ hour at room temperature and then hearted to about 40° C. under vacuum for 20 minutes to yield 34.5 g of a green liquid, p-toluene sulfinyl chloride. Thereafter, 34.43 g of p-toulene sulfinyl chloride were diluted into a 50 ml solution in toluene and stored under a nitrogen blanket for further use.

GENERAL PREPARATION OF EXAMPLES 4 AND 5

A glyphosate triester (0.015 mol), triethylamine (0.015 mol) as a hydrogen chloride acceptor, and 250 ml of toluene as an inert solvent were placed in an oven dried 500 ml flask. A solution of p-toluene sulfinyl chloride (0.015 mol) in toluene was then added slowly to the flask under nitrogen via syringe. The reaction was stirred at room temperature for 3 hours. Triethylamine hydrochloride, a precipitate, was removed by filtration, and the resulting toluene filtrate was concentrated in vacuo. The resulting oil was adsorbed onto silica gel and purified by HPLC on a 1"×4' silica gel column, to give the desired glyphosate sulfinamides, $^1$H NMR, $^{31}$P NMR, and elemental analyses were all consistent with pure material.

EXAMPLE 4

In this example, Glycine, N-[(Diphenoxyphosphinyl)methyl]-, phenylmethyl ester, was employed as a glyphosate reactant to prepare glycine, N-[(diphenoxyphosphinyl)methyl]-N-[(4-methylphenyl)sulfinyl]-, phenylmethyl ester as a yellow oil $n_D^{25}$ 1.5783, in 55% yield, corresponding to a compound of Formula (I) wherein R is phenyl, $R_1$ is 4-methylphenyl and $R_2$ in phenylmethyl. The analysis was:

Calculated: C 63.38; H, 5.14; N, 2.55; S, 5.83; Found: C, 63.68; H, 5.40; N, 2.47; S, 5.66.

EXAMPLE 5

In this example, Glycine, N-[[Bis(4-methoxyphenoxy)phosphinyl]methyl]-, ethyl ester was employed as a glyphosate reactant to prepare glycine, N-[[bis(4-methoxyphenoxy)phosphinyl]methyl]-N-[(4-methylphenyl)sulfinyl]-, ethyl ester as a yellow oil $n_D^{25}$ 1.5628, in 52% yield, corresponding to a compound of formula (I) wherein R is p-methoxyphenyl, $R_1$ is 4-methylphenyl and $R_2$ is ethyl. The analysis was Calculated: C, 57.03; H, 5.52; N, 2.56; S, 5.86; Found: C, 56.92; H, 5.50; N, 2.37; S, 5.44.

EXAMPLE 6

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |

| -continued | |
|---|---|
| Plant Response | Index |
| 100% control | 4 |

The plant species utilized in these tests are identified by letter in accordance with the following legend:

| A | Canada Thistle* | K | Barnyardgrass |
|---|---|---|---|
| B | Cocklebur | L | Soybean |
| C | Velvetleaf | M | Sugar Beet |
| D | Morningglory | N | Wheat |
| E | Lambsquarters | O | Rice |
| F | Smartweed | P | Sorghum |
| G | Yellow Nutsedge* | Q | Wild Buckwheat |
| H | Quackgrass* | R | Hemp Sesbania |
| I | Johnsongrass* | S | Panicum Spp |
| J | Downy Brome | T | Crabgrass |

*Established from vegetative propagules.

A dash (-) in the tables indicates that the particular species was absent in the test.

TABLE I

| Compound of Example No. | WAT | kg/h | A | B | C | D | E | F | G | H | I | J | K |
|---|---|---|---|---|---|---|---|---|---|---|---|---|---|
| 1 | 4 | 11.2 | 3 | 3 | 2 | 2 | 3 | 2 | 2 | 3 | 4 | 3 | 3 |
|   | 4 | 5.6  | 3 | 3 | 3 | 2 | 3 | 3 | 3 | 2 | 3 | 2 | 3 |
| 2 | 4 | 11.2 | 2 | 2 | 1 | 2 | 3 | 2 | 2 | 3 | 1 | 1 | 3 |
|   | 4 | 5.6  | 2 | 2 | 1 | 2 | 3 | 1 | 2 | 1 | 3 | 0 | 3 |
| 3 | 4 | 11.2 | 3 | 2 | 1 | 2 | 3 | 1 | 2 | 3 | 3 | 1 | 3 |
|   | 4 | 5.6  | 0 | 1 | 1 | 2 | 3 | 4 | 2 | 2 | 2 | 1 | 3 |
| 4 | *4 | 11.2 | — | 2 | 1 | 2 | 0 | 0 | 2 | 0 | 2 | 0 | 2 |
|   | *4 | 5.6  | — | 2 | 1 | 1 | 0 | 0 | 2 | 3 | 2 | 0 | 2 |
| 5 | 4 | 11.2 | — | 1 | 0 | 1 | 3 | 0 | 1 | 0 | 0 | 1 | 1 |
|   | 2 | 5.6  | — | 0 | 0 | 0 | 0 | 0 | 1 | 0 | 0 | 0 | 0 |

| Compound of Example No. | WAT | kg/h | L | M | N | O | B | Q | D | R | E | F | C | J | S | K | T |
|---|---|---|---|---|---|---|---|---|---|---|---|---|---|---|---|---|---|
| 1 | 4 | 5.6  | 2 | 2 | 2 | 1 | 2 | 3 | 2 | 3 | 3 | 3 | 3 | 2 | 2 | 3 | 3 |
|   | 4 | 1.12 | 1 | 1 | 1 | 0 | 2 | 2 | 1 | 2 | 0 | 1 | 1 | 0 | 2 | 2 | 2 |
|   | 2 | 0.28 | 1 | 0 | 1 | 0 | 1 | 0 | 1 | 1 | 1 | 0 | 0 | 0 | 0 | 0 | 0 |
| 2 | 4 | 5.6  | 1 | 1 | 2 | 0 | 2 | 2 | 2 | 2 | 2 | 3 | 1 | 0 | 1 | 2 | 3 |
|   | 4 | 1.12 | 1 | 0 | 1 | 0 | 1 | 1 | 0 | 1 | 0 | 1 | 0 | 0 | 0 | 1 | 2 |
|   | 2 | 0.28 | 1 | 0 | 0 | 0 | 0 | 0 | 0 | 1 | 0 | 0 | 0 | 0 | 0 | 0 | 1 |
| 3 | 4 | 5.6  | 1 | 2 | 2 | 0 | 3 | 2 | 2 | 2 | 1 | 4 | — | 2 | 2 | 3 | 4 |
|   | 4 | 1.12 | 1 | 1 | 2 | 0 | 2 | 1 | 1 | 2 | 0 | 3 | 1 | 1 | 1 | 2 | 3 |
|   | 2 | 0.28 | 0 | 0 | 0 | 0 | 0 | 1 | 0 | 1 | 0 | 1 | 0 | 0 | 0 | 1 | 1 |
| 4 | 4 | 5.6  | 1 | 3 | 1 | 1 | 1 | 3 | 3 | 2 | 1 | 0 | 1 | 2 | 1 | 2 | 3 |
|   | 4 | 1.12 | 0 | 0 | 0 | 0 | 1 | 2 | 2 | 1 | 0 | 1 | 0 | 0 | 1 | 1 | 1 |
|   | 4 | 0.28 | 0 | 0 | 0 | 0 | 0 | 0 | 2 | 1 | 1 | 1 | 1 | 0 | 1 | 0 | 1 |

*Sprayed in 100 gallon per acre THF immediately after formulation

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the composition of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific illustrative herbicidal compositions of this invention. While these herbicidal compositions have not been actually prepared, they are hereinafter listed since they are believed consistent with the inventive concept.

| | | |
|---|---|---|
| 1. | Glycine, N—[(diphenoxy-phosphinyl)methyl]-N—(phenylsulfinyl)-, methyl ester | 25 parts |
| | Nonylphenol + 10EO | 2 parts |
| | Igepon T-73 | 2 parts |
| | Amorphous Silica | 71 parts |
| | The components are blended and ground to give a fine powder. Sufficient surfactant, such as Tween 20, nonyl phenyl polyoxyethylene ether, ethoxylate soya amine, etc., is added to the spray solution preferably to give a concentration of about 0.25–0.5%. | |
| 2. | Glycine, N—([bis(4-methoxyphenoxy)phosphinyl)-methyl]-N—[(4-methyl-phenyl)sulfinyl]-, ethyl ester | 5 parts |
| | Aerosol OTB | 1 part |
| | Kaolin | 94 parts |
| | The components are blended and ground to a fine powder which is applied as a dust. | |
| 3. | Glycine, N—[(diphenoxy-phosphinyl)methyl]-N—[(4-methylphenyl)sulfinyl]-, phenylmethyl ester | 24 parts |
| | Calcium dodecylbenzene sulfonate | 2 parts |
| | Octylphenyl polyoxyethylene ether | 7 parts |
| | Butyl acetate | 66 parts |
| 4. | Glycine, N—[(diphenoxy-phosphinyl)methyl]-N—(phenylsulfinyl)-, phenyl-methyl ester | 20 parts |
| | Isopropylammonium dodecylbenzene sulfonate | 3.5 parts |
| | Caster oil polyoxyethylene ether | 2.5 parts |
| | Nonylphenyl polyoxyethylene ether | 4 parts |
| | Chloroform | 70 parts |
| 5. | Glycine, N—([bis(4-methoxy-phenoxy)phosphinyl]methyl)-N—(phenylsulfinyl)-, ethyl ester | 5 parts |
| | Tween 80 | 3 parts |
| | Methyl isobutyl ketone | 92 parts |
| | In applying the herbicide compositions above, using spray solutions it may be desirable to add additional surfactants including Tween 20, Nonyl phenyl polyoxyethylene ether, ethoxylate soya amine, and the like to the tank to obtain maximum phytotoxicity. | |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Alabama U.S.A., the teachings of which are incorporated herein by reference in their entirety.

Another method of possibly applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound and composition employed may determine to a large extent the particular application method employed therewith.

The aforementioned and other possible methods for applying liquid compositions to plants are discussed in detail in "Rope Wick Applicator—Tool With A Future", Dale, James E., pp. 3–4, "The Recirculating Sprayer and Roundup® Herbicide", Derting, Claude W., pp. 5–7, and "C.D.A. Herbicide Application", McGarvey, Frank X., *Weeds Today,* Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises contacting said plants or plant growth medium with a herbicidally effective amount of a compound of the formula 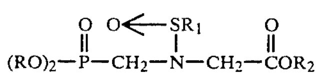 wherein R is selected from the group consisting of phenyl, naphthyl or biphenylyl; or phenyl, naphthyl or biphenylyl substituted with from 1 to 3 substituents independently selected from the group consisting of hydrogen, lower alkyl, lower alkoxy and methylenedioxy, $R_1$ is independently phenyl or phenyl substituted with from one to three substituents selected from the group consisting of lower alkyl, lower alkoxy, halogen, trifluoromethyl, cyano and nitro and wherein $R_2$ is lower alkyl or araloweralkyl.

2. A method according to claim 1 wherein R is phenyl or phenyl substituted with from 1 to 3 substituents independently selected from the group consisting of hydrogen, lower alkyl and lower alkoxy.

3. A method of claim 2 wherein $R_2$ is lower alkyl, or aralower alkyl.

4. A method according to claim 3 wherein $R_1$ is phenyl or phenyl substituted with from 1 to 3 substituents independently selected from the group consisting of lower alkyl and lower alkoxy.

5. A method according to claim 4 wherein the compound is glycine, N-[(diphenoxyphosphinyl)methyl]-N-(phenyl-sulfinyl)-, methyl ester.

6. A method according to claim 4 wherein the compound is glycine, N-[[bis(4-methoxyphenoxy)phosphinyl]-methyl]-N-(phenylsulfinyl)-, ethyl ester.

7. A method according to claim 4 wherein the compound is glycine, N-[(diphenoxyphosphinyl)methyl]-N-(phenylsulfinyl)-, phenylmethyl ester.

8. A method according to claim 4 wherein the compound is glycine, N-[(diphenoxyphosphinyl)methyl]-N-[(4-methylphenyl)sulfinyl]-, phenylmethyl ester.

9. A method according to claim 4 wherein the compound is glycine, N-[[bis(4-methoxyphenoxy)phosphinyl)-methyl]-N-[(4-methylphenyl)sulfinyl]-, ethyl ester.

10. A compound of the formula 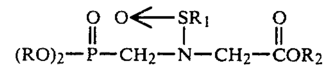 wherein R is selected from the group consisting of phenyl, naphthyl or biphenylyl; or phenyl, naphthyl or biphenylyl substituted with from 1 to 3 substituents independently selected from the group consisting of hydrogen, lower alkyl, lower alkoxy, methylenedioxy; $R_1$ is independently phenyl or phenyl substituted with from one to three substituents selected from the group consisting of lower alkyl, lower alkoxy, halogen, trifluoromethyl, cyano, nitro and halogen and wherein $R_2$ is lower alkyl or araloweralkyl.

11. A compound of claim 10 wherein R is phenyl or phenyl substituted with from 1 to 3 substituents indpendently selected from the group consisting of hydrogen, lower alkyl and lower alkoxy.

12. A compound of claim 11 wherein $R_1$ is phenyl or phenyl substituted with from 1 to 3 substituents independently selected from the group consisting of lower alkyl and lower alkoxy.

13. A compound of claim 12 wherein $R_2$ is lower alkyl or aralower alkyl.

14. A compound of claim 13 wherein the compound is glycine, N-[(diphenoxyphosphinyl)methyl]-N-(phenylsulfinyl)-, methyl ester.

15. A compound according to claim 13 wherein the compound is glycine, N-[[bis(4-methoxyphenoxy)phosphinyl]-methyl]-N-(phenylsulfinyl)-, ethyl ester.

16. A compound according to claim 13 wherein the compound is glycine, N-[(diphenoxyphosphinyl)methyl]-N-(phenylsulfinyl)-, phenylmethyl ester.

17. A compound according to claim 13 wherein the compound is glycine, N-[(diphenoxyphosphinyl)methyl]-N-[(4-methylphenyl)sulfinyl]-, phenylmethyl ester.

18. A compound according to claim 13 wherein the compound is glycine, N-[[bis(4-methoxyphenoxy)phosphinyl]-methyl]-N-[(4-methylphenyl)sulfinyl]-, ethyl ester.

19. A herbicidal composition comprising an inert adjuvant and a herbicidally effective amount of a compound of the formula wherein R selected from the group consisting of phenyl, naphthyl or biphenylyl; or phenyl, naphthyl or biphenylyl substituted with from 1 to 3 substituents independently selected from the group consisting of hydrogen, lower alkyl, lower alkoxy, and methylenedioxy, $R_1$ is independently phenyl or phenyl substituted with from one to three substituents selected from the group consisting of lower alkyl, lower alkoxy, cyano, halogen, trifluoromethyl and nitro and wherein $R_2$ is lower alkyl or araloweralkyl.

20. A composition according to claim 19 wherein R is phenyl or phenyl substituted with from 1 to 3 substituents independently selected from the group consisting of hydrogen, lower alkyl and lower alkoxy.

21. A composition according to claim 20 wherein $R_1$ is phenyl or phenyl substituted with from 1 to 3 substituents independently selected from the group consisting of lower alkyl and lower alkoxy.

22. A composition of claim 20 wherein $R_2$ is lower alkyl or aralower alkyl.

23. A composition according to claim 22 wherein the compound is glycine, N-[(diphenoxyphosphinyl)methyl]-N-(phenylsulfinyl)-, methyl ester.

24. A composition according to claim 22 wherein the compound is glycine, N-[[bis(4-methoxyphenoxy)phosphinyl]-methyl]-N-(phenylsulfinyl)-, ethyl ester.

25. A composition according to claim 22 wherein the compound is glycine, N-[(diphenoxyphosphinyl)methyl]-N-(phenylsulfinyl)-, phenylmethyl ester.

26. A composition according to claim 22 wherein the compound is glycine, N-[(diphenoxyphosphinyl)methyl]-N-[(4-methylphenyl)sulfinyl]-, phenylmethyl ester.

27. A composition according to claim 22 wherein the compound is glycine, N-[[bis(4-methoxyphenoxy)phosphinyl]-methyl]-N-[(4-methylphenyl)sulfinyl]-, ethyl ester.

* * * * *

UNITED STATES PATENT AND TRADEMARK OFFICE
CERTIFICATE OF CORRECTION

PATENT NO. : 4,405,356

DATED : September 20, 1983

INVENTOR(S) : JAMES A. SIKORSKI ET AL

It is certified that error appears in the above-identified patent and that said Letters Patent is hereby corrected as shown below:

Column 7, line 38 "L M N O B Q D R E F L J S K T"

should read --L M N O P B Q D R E F L J S K T--.

Signed and Sealed this

Twenty-second Day of November 1983

[SEAL]

Attest:

GERALD J. MOSSINGHOFF

Attesting Officer

Commissioner of Patents and Trademarks